(12) United States Patent
Yamada et al.

(10) Patent No.: US 6,613,339 B1
(45) Date of Patent: Sep. 2, 2003

(54) NAIL COSMETICS

(75) Inventors: Hideyuki Yamada, Fukui (JP); Keiko Yamasaki, Kagawa (JP); Keiji Nozaki, Tokyo (JP)

(73) Assignees: Teikoku Seiyaku Co., Ltd., Kagawa (JP); Seiren Co., Ltd., Fukui (JP)

( * ) Notice: Subject to any disclaimer, the term of this patent is extended or adjusted under 35 U.S.C. 154(b) by 0 days.

(21) Appl. No.: 09/830,115
(22) PCT Filed: Jul. 31, 2000
(86) PCT No.: PCT/JP00/05125

§ 371 (c)(1),
(2), (4) Date: Jul. 18, 2001

(87) PCT Pub. No.: WO01/15660
PCT Pub. Date: Mar. 8, 2001

(30) Foreign Application Priority Data

Aug. 30, 1999 (JP) .......................................... 11-242454

(51) Int. Cl.$^7$ .............................. A61K 7/00; A61K 7/04
(52) U.S. Cl. ........................................ 424/401; 424/61
(58) Field of Search .................................. 424/401, 61

(56) References Cited

U.S. PATENT DOCUMENTS 3,552,401 A * 1/1971 Michaelson .................. 132/73

* cited by examiner

*Primary Examiner*—Thurman K. Page
*Assistant Examiner*—S. Howard
(74) *Attorney, Agent, or Firm*—Wenderoth, Lind & Ponack, L.L.P.

(57) ABSTRACT

An object of the present invention is to provide a cosmetic for nail that suppresses dryness of nails, that makes nails hard to fracture, that makes nails glossy as they are, that keeps or improves healthiness of nails, and that is highly safe. The cosmetic for nail is provided by adding 0.02 to 20% by weight of sericin as an effective ingredient additionally to the conventional cosmetic ingredients.

15 Claims, No Drawings

NAIL COSMETICS

This application is a 371 of PCT/JP00/05125 filed Jul. 31, 2000.

TECHNICAL FIELD

The present invention relates to a cosmetic for nail for preferable use in suppressing dryness of nails, keeping moisture, and making nails glossy and, more specifically, to a cosmetic for nail that excels in protecting nails and preserving or improving healthiness of nails.

BACKGROUND ART

A nail is a thin corneous layer forming from epidermis of the dorsal side of the fingers or toes, and is indispensable for our daily life. Nails enable us to seize by the tip of the fingers and to carry out precise work. On the other hand, nails are noticeable in the hand, are considered as an important point in beauty treatment. In modern life, nails are considered as one portion of the total beauty treatment, and beauty salons specializing in nail care come out. People interested in nails have increased year by year.

As a result, nowadays many kinds of cosmetics for nail have been sold, and many women use these cosmetics. However, repeated use of cosmetics for nail (nail polish and the like) or a nail polish remover makes nails dry and brittle to lose glossiness day by day. Thus, it is expected to develop a cosmetic for nail that moisturizes nails, protects nails, and keep healthiness of nails. Nowadays a main line in cosmetics for nail has been one containing moisture preserving ingredients such as collagen, amino acids and keratin to supplement nails with moisture.

However, since these moisture preserving ingredients have no coat forming ability, moisture preserving effect for moisture lost by a nail polish remover is weak, and these cannot improve dryness and cracks of nails. In the case of using a cream-type cosmetic that is rich in oily components to supplement nails with moisture, there are many problems, for example, it takes a long time to dry off after coating, it is very sticky, and when touching something, oily components attach it to dirty it. Thus, it is expected to improve such cosmetics.

DISCLOSURE OF THE INVENTION

It is an object of the present invention to provide a cosmetic for nail that suppresses dryness of nails, that makes nails hard to fracture, that makes nails glossy as they are, that keeps or improves healthiness of nails, and that is highly safe.

In light of the above object, the present inventors have made intensive studies to find out that a cosmetic containing sericin excels in effects that suppress dryness of nails, that make nails glossy appropriately, and that keep or improve healthiness of nails. The present invention has been completed on the basis of this finding.

That is, the present invention relates to a cosmetic for nail comprising sericin as an effective ingredient.

The present invention also relates to a cosmetic for nail, wherein the content of sericin in the cosmetic for nail is 0.02 to 20% by weight to whole the amount of the cosmetic.

The present invention is further described in detail below.

The cosmetic of the present invention is characterized by containing sericin as an effective ingredient.

Sericin is a naturally occurring protein obtained by extracting from silk. It has been known that sericin excels in hygroscopicity, water absorbing ability, and coat forming ability. However, there has been no example used in a cosmetic for nail as in the present invention. It is unexpected that a cosmetic for nail containing sericin shows remarkable effects that improve moisture preserving ability of nails, and that make nails glossy. In the case of using only proteins except sericin such as collagen and keratin as a protein component, it shows drawbacks that coat forming ability is weak, and nail moisture preserving effect and nail protecting effect are not obtained.

Sericin used in the present invention may be obtained by any methods. Preferable sericin is obtained by partial hydrolysis of sericin contained in silk fiber by the use of chemical purifying method or enzymatic purifying method to elute the sericin, thereby subsequently precipitating by the use of chemicals. A product containing 20 to 40% serine is particularly preferable.

Sericin is usually powdery but easily water-soluble, and it remains stable as an aqueous solution. Sericin is excellent in miscibility with conventional cosmetic ingredients, and in safety because of no side effects against skin. Therefore sericin can be used appropriately in combination with conventional cosmetic ingredients such as various surfactants, emulsifying ingredients, stabilizers, organic acids, fats and oils, alcohols, vitamins, aseptics, and perfumes.

The cosmetic for nail of the present invention contains the above described sericin as an effective ingredient. The cosmetic for nail of the present invention may be a liquid preparation or a patch-type sheet preparation. Examples of the liquid preparation include nail enamels, nail basecoats, nail treatments, removers, nail lotions and nail creams. Examples of the patch-type sheet preparation include nail care sheet packs and nail treatment sheet packs.

The content of sericin in the cosmetic for nail is preferably 0.02 to 20% by weight, more preferably 0.05 to 10% by weight, to whole the amount of the cosmetic. If the content is lower than 0.02% by weight, protecting effect against nail is weak. If the content excels 20% by weight, it is uneconomical because the amount of sericin that is not contributive to nail protection becomes great.

In the cosmetic for nail of the present invention, besides the above sericin which is an essential ingredient, various ingredients for use in conventional cosmetics may be contained optionally. Examples of such optional ingredients include, for example, hydrocarbons such as petrolatum and squalane; aseptics such as methyl paraben, propyl paraben and butyl paraben; oils such as jojoba oil, castor oil and olive oil; fatty acids such as stearic acid and oleic acid; higher alcohols such as cetyl alcohol and oleil alcohol; various surfactants such as non-ionic surfactants such as polyoxyethylene sorbitan fatty acid ester and polyoxyethylene hardened castor oil, anionic surfactants, cationic surfactants and amphoteric surfactants; polyhydric alcohols such as glycols such as propylene glycol, 1,3-butylene glycol, dipropylene glycol and polyethylene glycol and glycerol; ethers such as polyoxyethylene isocetyl ether; water-soluble polymeric compounds such as carboxyvinyl polymer, poly(acrylic acid), sodium polyacrylate, sodium carmellose, polyvinyl alcohol, polyvinylpyrrolidone; saccharides such as polysaccharide such as hyaluronic acid and chitosan, D-glucose and D-fructose; ethanol, emulsifying ingredients, stabilizers, ultraviolet absorbers, antioxidants, various vitamins, medicinal properties, perfumes, coloring matters, and powders. Proteins except sericin such as collagen, elastin and keratin can be used together with sericin for use in the present invention.

The addition amount of these various ingredients can be decided depending on kinds of the respective products. These various ingredients can be formed as a cosmetic by conventional methods.

BEST MODE OF CARRYING OUT THE INVENTION

The present invention is illustrated in further detail by the following examples, but the present invention is not limited to the examples. All percentages in examples and comparative examples are by weight.

EXAMPLES 1 AND 2, COMPARATIVE EXAMPLES 1 AND 2

(1) Preparation of nail treatments

Nail treatments and patches were prepared for which prescriptions are as shown in the following Table 1 to 4.

Example 1

Nail treatment

TABLE 1

| | |
|---|---|
| Sericin | 3.0% |
| Clycerol | 2.0 |
| Dipropylene glycoi | 3.0 |
| Polyoxyethylene isocetyl ether | 1.0 |
| Ethanol | 4.0 |
| Aseptic | adequate amount |
| Perfume | adequate amount |
| Purified water | adequate amount |
| Whole amount | 100 |

Example 2

Patch (Nail treatment sheet pack)

TABLE 2

| | |
|---|---|
| Sericin | 2.0% |
| Sodium polyacrylate | 5.0 |
| Sodium carmellose | 5.0 |
| Glycerol | 15.0 |
| Castor oil | 1.0 |
| Dried aluminum hydroxide gel | O.06 |
| Aseptic | adequate amount |
| Perfume | adequate amount |
| Purified water | adequate amount |
| Whole amount | 100 |

Comparative Example 1

Nail treatment

TABLE 3

| | |
|---|---|
| Collagen | 3.0% |
| Glycerol | 2.0 |
| Dipropylene glycol | 3.0 |
| Polyoxyethylene isocetyl ether | 1.0 |
| Ethanol | 8.0 |
| Aseptic | adequate amount |
| Perfume | adequate amount |
| Purified water | adequate amount |
| Whole amount | 100 |

Comparative Example 2

Patch (Nail treatment sheet pack)

TABLE 4

| | |
|---|---|
| Collagen | 2.0% |
| Sodium polyacrylate | 5.0 |
| Sodium carmellose | 5.0 |
| Glycerol | 15.0 |
| Castor oil | 1.0 |
| Dried aluminum hydroxide gel | 0.06 |
| Aseptic | adequate amount |
| Perfume | adequate amount |
| Purified water | adequate amount |
| Whole amount | 100 |

(2) Evaluation

Sensory tests were carried out against 30 female panelists who usually use nail polishes, nail polish removers and the like, and usually complain dryness, fractures, and lack of glossiness of nails. That is, examinees (female panelists) applied a manicure and subsequently removed with a nail polish remover, then the nail treatments of the above (Example 1) and (Comparative Example 1) were coated. Concerning the above (Example 2) and (Comparative Example 2), after those patches were patched for an hour, then they were peeled away. This is continued for a month and condition of nails was observed to evaluate the results in terms of the respective evaluation items (1. dryness of nails, 2. fractures of nails, 3. gloss of nails) based on the following standards. The evaluation results are shown in Table 5. Numbers in Table 5 stand for headcount of the respective evaluation.

1. Dryness of nails
   −: not noticeable
   ±: a little noticeable
   +: noticeable
2. Fractures of nails
   −: noticeable
   ±: a little noticeable
   +: not noticeable
3. Gloss of nails
   −: positive
   ±: a little
   +: negative

TABLE 5

| Evaluation item | Standards | Example 1 | Example 2 | Comparative Example 1 | Comparative Example 2 |
|---|---|---|---|---|---|
| Dryness of nails | − | 29 | 30 | 0 | 0 |
| | ± | 1 | 0 | 0 | 0 |
| | + | 0 | 0 | 30 | 30 |
| Fracture of nails | − | 0 | 0 | 30 | 30 |
| | ± | 2 | 6 | 0 | 0 |
| | + | 28 | 24 | 0 | 0 |
| Gloss of | − | 28 | 30 | 0 | 0 |
| | ± | 2 | 0 | 0 | 0 |
| | + | 0 | 0 | 30 | 30 |

EXAMPLE 3 AND COMPARATIVE EXAMPLE 3

(1) Preparation of nail basecoat

Nail basecoats were prepared for which prescriptions are as shown in the following Table 6 and 7.

Example 3

TABLE 6

| Sericin | 4.0% |
|---|---|
| Polyethylene glycol 400 | 1.0 |
| Dipropylene glycol | 3.0 |
| Polyoxyethylene hardened castor oil | 1.0 |
| Ethanol | 6.0 |
| Aseptic | adequate amount |
| Perfume | adequate amount |
| Purified water | adequate amount |
| Whole amount | 100 |

Comparative Example 3

TABLE 7

| Collagen | 4.0% |
|---|---|
| Polyethylene glycol 400 | 1.0 |
| Dipropylene glycol | 3.0 |
| Polyoxyethylene hardened castor oil | 1.0 |
| Ethanol | 6.0 |
| Aseptic | adequate amount |
| Perfume | adequate amount |
| Purified water | adequate amount |
| Whole amount | 100 |

(2) Evaluation

Sensory tests were carried out against 30 female panelists who usually use nail polishes, nail polish removers and the like, and usually complain dryness, fractures, and lack of glossiness of nails. That is, examinees (female panelists) applied the nail basecoats of the above (Example 3) and (Comparative Example 3), then subsequently used a nail polish. This is continued for a month and condition of nails was observed to evaluate the results in terms of the respective evaluation items (1. dryness of nails, 2. fractures of nails, 3. gloss of nails) based on the following standards. The evaluation results are shown in Table 8. Numbers in Table 8 stand for headcount of the respective evaluation.

1. Dryness of nails
  −: not noticeable
  ±: a little noticeable
  +: noticeable
2. Fractures of nails
  −: noticeable
  ±: a little noticeable
  +: not noticeable
3. Gloss of nails
  −: positive
  ±: a little
  +: negative

TABLE 8

| Evaluation item | Standards | Example 3 | Comparative Example 3 |
|---|---|---|---|
| Dryness of nails | − | 28 | 0 |
|  | ± | 2 | 0 |
|  | + | 0 | 30 |
| Fracture of nails | − | 0 | 22 |
|  | ± | 2 | 8 |
|  | + | 28 | 0 |
| Gloss of nails | − | 27 | 0 |
|  | ± | 3 | 0 |
|  | + | 0 | 30 |

INDUSTRIAL APPLICABILITY

Sericin, which is a necessitated ingredient of the cosmetic for nail of the present invention, excels in nail protecting function, so that it suppresses dryness of nails, makes nails hard to fracture, and makes nails glossy as they are. Sericin also remedies remarkably nails damaged by manicure products, a nail polish remover or the like. Sericin is also useful for base coats of manicure products and the like. Moreover, since being made of natural silk, sericin excels in safety and exhibit effects that no other cosmetics for nail show. Thus, the cosmetic for nail of the present invention containing sericin as an effective ingredient enables keeping or improving healthiness of nails.

What is claimed is:

1. A cosmetic composition for a human nail, comprising sericin as an effective ingredient, and at least one other ingredient selected from the group consisting of polyhydric alcohols and water-soluble polymeric compounds, wherein the content of sericin is 0.02 to 20% by weight based upon the total weight of the cosmetic composition.

2. The cosmetic composition according to claim 1, wherein the content of sericin is 0.05 to 10% by weight based upon the total weight of the cosmetic composition.

3. The cosmetic composition according to claim 1, wherein the content of sericin is 0.02 to 4% by weight based upon the total weight of the cosmetic composition.

4. The cosmetic composition according to claim 1, which is in the form of a liquid preparation.

5. The cosmetic composition according to claim 1, which is in the form of a patch sheet preparation.

6. A cosmetic composition applied to a human nail, comprising sericin as an effective ingredient, and at least one other ingredient selected from the group consisting of polyhydric alcohols and water-soluble polymeric compounds, wherein the content of sericin is 0.02 to 20% by weight based upon the total weight of the cosmetic composition.

7. The cosmetic composition according to claim 6, wherein the content of sericin is 0.05 to 10% by weight based upon the total weight of the cosmetic composition.

8. The cosmetic composition according to claim 6, wherein the content of sericin is 0.02 to 4% by weight based upon the total weight of the cosmetic composition.

9. The cosmetic composition according to claim 6, which is in the form of a liquid preparation.

10. The cosmetic composition according to claim 6, which is in the form of a patch sheet preparation.

11. A method for preserving or improving the healthiness of a human nail, which comprises applying the cosmetic composition according to claim 1 to the human nail.

12. A method for preserving or improving the healthiness of a human nail, which comprises applying the cosmetic composition according to claim 2 to the human nail.

13. A method for preserving or improving the healthiness of a human nail, which comprises applying the cosmetic composition according to claim 3 to the human nail.

14. A method for preserving or improving the healthiness of a human nail, which comprises applying the cosmetic composition according to claim 4 to the human nail.

15. A method for preserving or improving the healthiness of a human nail, which comprises applying the cosmetic composition according to claim 5 to the human nail.

* * * * *